US006875773B1

(12) United States Patent
Dunn et al.

(10) Patent No.: US 6,875,773 B1
(45) Date of Patent: Apr. 5, 2005

(54) COMBINATION THERAPY FOR TREATMENT OF FIV INFECTION

(76) Inventors: Ben M. Dunn, College of Medicine, Health Science Center, P.O. Box 100245, Gainesville, FL (US) 32610-0245; Janet K. Yamamoto, University of Florida, College of Veterinary Medicine, P.O. Box 110880, Gainesville, FL (US) 32611-0880; Maki Arai, University of Florida, College of Veterinary Medicine, P.O. Box 100145, Gainesville, FL (US) 32610

( * ) Notice: Subject to any disclaimer, the term of this patent is extended or adjusted under 35 U.S.C. 154(b) by 0 days.

(21) Appl. No.: 09/763,037

(22) PCT Filed: May 28, 1999

(86) PCT No.: PCT/US99/11940

§ 371 (c)(1),
(2), (4) Date: Jul. 24, 2001

(87) PCT Pub. No.: WO99/60988

PCT Pub. Date: Dec. 2, 1999

Related U.S. Application Data

(60) Provisional application No. 60/087,281, filed on May 29, 1998.

(51) Int. Cl.[7] .............................................. A61K 31/505
(52) U.S. Cl. ........................ 514/274; 514/256; 514/269
(58) Field of Search ................................ 514/256, 269, 514/274

(56) References Cited

FOREIGN PATENT DOCUMENTS

| DE | 197 03 131 A1 | 7/1998 |
|----|---------------|--------|
| WO | WO 96/22778 A1 | 8/1996 |
| WO | WO 96/23509 A1 | 8/1996 |
| WO | WO 96/30025 A1 | 10/1996 |
| WO | WO 97/03055 A1 | 1/1997 |
| WO | WO 97/49411 A1 | 12/1997 |
| WO | WO 99/55372 A1 | 11/1999 |
| WO | WO 99/66936 A1 | 12/1999 |

OTHER PUBLICATIONS

Goodman & Gilman's, The Pharmacological Basis of Therapeutics, Ninth Edition, McGraw–Hill, New York, (1996), Chapter 50, p. 1192.*
CAPLUS, DN 123:102047, Budt et al., Bioorganic & Medicinal Chemistry (1995), 3(5), 559–71 (abstract only).*
Boucher, C. A. B. et al. "High–Level Resistance to (−) Enantiomeric 2'–Deoxy –3'—Thiacytidine In Vitro Is Due to One Amino Acid Substitution in the Catalytic Site of Human Immunodeficiency Virus Type 1 Reverse Transcriptase" *Antimicrobial Agents And Chemotherapy,* Oct. 1993, pp. 2231–2234, vol. 37, No. 10.
Deeks, S. G. et al. "HIV–1 Protease Inhibitors" *JAMA,* Jan. 8, 1997, pp. 145–153, vol. 277, No. 2.

Dunn, B. M. et al. "Subsite Preferences of Retroviral Proteinases" *Methods in Enzymology,* 1994, pp. 254–278, vol. 241, Academic Press, Inc.
Gardner, M. B. "Simian and Feline Immunodeficiency Viruses: Animal Lentivirus Models for Evaluation of AIDS Vaccines and Antiviral Agents" *Antiviral Research,* 1991, pp. 267–286, vol. 15, Elsevier Science Publishers B.V.
Harrigan, R. "Measuring Viral Load in the Clinical Setting" *Journal of Acquired Immune Deficiency Syndromes and Human Retrovirology,* 1995, pp. S34–S40, vol. 10 (Suppl. 1), Lippincott–Raven Publishers, Philadelphia.
Hart, S. et al. "Long–Term Treatment of Diseased, FIV–Seropositive Field Cats with Azidothymidine (AZT)" *J. Vet. Med. A.,* 1995, pp. 397–409, vol. 42, Blackwell Wissenschafts, Verlag, Berlin.
Hartmann, K. et al. "Use of Two Virustatica (AZT, PMEA) in the Treatment of FIV and of FeLV Seropositive Cats with Clinical Symptoms" *Veterinary Immunology and Immunopathology,* 1992, pp. 167–175, vol. 35, Elsevier Science Publishers B.V., Amsterdam.
Hayes, K. A. et al. "Prophylactic ZDV Therapy Prevents Early Viremia and Lymphocyte Decline But Not Primary Infection In Feline Immunodeficiency Virus–Inoculated Cats" *Journal of Acquired Immune Deficiency Syndromes,* 1993, pp. 127–134, vol. 6, Raven Press, Ltd., New York.
Hayes, K. A. et al. "Early Suppression of Viremia by ZDV Does Not Alter the Spread of Feline Immunodeficiency Virus Infection in Cats" *Journal of Acquired Immune Deficiency Syndromes and Human Retrovirology,* 1995, pp. 114–122, vol. 9, No. 2, Raven Press. Ltd., New York.
Johnson, C. M. et al. "FIV as a Model for AIDS Vaccination" *AIDS Research and Human Retroviruses,* 1994, pp. 225–228, vol. 10, No. 3, Mary Ann Liebert, Inc., Publishers.
Katlama, C. "Combination 3TC (Lamivudine)/ ZDV (Zidovudine) Vs. ZVD Monotherapy in ZVD Naive HIV–1 Positive Patients With CD4 of 100–400 Cells/mm$^3$, Abstr" *AIDS,* 1994, p. 56, vol. 8 (Suppl. 4).
Lange, J. M. A. "Triple Combinations: Present and Future" *Journal of Acquired Immune Deficiency Syndromes and Human Retrovirology,* 1995, pp. S77–S82, vol. 10 (Supp. 1), Lippincott–Raven Publishers, Philadelphia.

(Continued)

*Primary Examiner*—Christopher S. F. Low
*Assistant Examiner*—C. Delacroix-Muirheid
(74) *Attorney, Agent, or Firm*—Saliwanchik, Lloyd & Saliwanchik

(57) ABSTRACT

The present invention pertains to methods for therapeutic and prophylactic treatment of cats against FIV infection. Methods of the present invention utilize a combination of antiretroviral compounds to treat or prevent FIV infection in a feline animal. In one embodiment, the method comprises administering an effective amount of AZT and another nucleoside analog, such as, for example, 3TC to the animal. In another embodiment, cats are given an effective dose(s) of AZT, 3TC, and a retroviral protease inhibitor.

14 Claims, 7 Drawing Sheets

OTHER PUBLICATIONS

Larder, B. A. "Viral Resistance and the Selection of Antiretroviral Combinations" *Journal of Acquired Immune Deficiency Syndromes and Human Retrovirology*, 1995, pp. S28–S33, vol. 10 (Suppl. 1), Lippincott–Raven Publishers, Philadelphia.

Magnani, M. et al. "Feline Immunodeficiency Virus Infection of Macrophages: In Vitro and in Vivo Inhibition by Dideoxycytidine–5'–triphosphate–Loaded Erythrocytes" *AIDS Research and Human Retroviruses*, 1994, pp. 1179–1186, vol. 10, No. 9, Mary Ann Liebert, Inc., Publishers.

Meers, J. et al. "Feline Immunodeficiency Virus Infection: Plasma, but not Peripheral Blood Mononuclear Cell Virus Titer is Influenced by Zidovudine and Cyclosporine" *Arch Virol*, 1993, pp. 67–81, vol. 132.

Newell, M. L. et al. "A Risk–Benefit Assessment of Zidovudine in the Prevention of Perinatal HIV Transmission" *Drug Safety*, 1995, pp. 274–281, vol. 12, No. 4.

North, T. W. et al. "Feline Immunodeficiency Virus, a Model for Reverse Transcriptase–Targeted Chemotherapy for Acquired Immune Deficiency Syndrome" *Antimicrobial Agents and Chemotherapy*, Jun. 1989, pp. 915–919, vol. 33, No. 6, American Society for Microbiology.

Paul, D. B. et al. "Short–Term Stability of HIV Provirus Levels in the Peripheral Blood of HIV–Infected Individuals" *Journal of Medicinal Virology*, 1995, pp. 292–297, vol. 47, Wiley–Liss, Inc.

Pedersen, N. C. et al. "Isolation of a T–Lymphotropic Virus from Domestic Cats with an Immunodeficiency–Like Syndrome" *Science*, 1987, pp. 790–793, vol. 235.

Philpott, M. S. et al. "Evaluation of 9–(2–Phosphonylmethoxyethyl) Adenine Therapy for Feline Immunodeficiency Virus Using a Quantitative Polymerase Chain Reaction" *Veterinary Immunology and Immunopathology*, 1992, p. 155–166, vol. 35, Elsevier Science Publishers B. V., Amsterdam.

Siebelink, K. H.J. et al. "Feline Immunodeficiency Virus (FIV) Infection in the Cat as a Model for HIV Infection in Man: FIV–Induced Impairment of Immune Function" *AIDS Research and Human Retroviruses*, 1990, pp. 1373–1378, vol. 6, No. 12, Mary Ann Liebert, Inc., Publishers.

Smith, R. A. et al. "A Novel Point Mutation at Position 156 of Reverse Transcriptase from Feline Immunodeficiency Virus Confers Resistance to the Combination of (–)-β2', 3'–Dideoxy–3'–Thiacytidine and 3'–Azido–3'–Deoxythymidine" *Journal of Virology*, 1998, pp. 2335–2340, vol. 72, No. 3.

Smith, R. A. et al. "A Novel Met–to–Thr Mutation in the YMDD Motif of Reverse Transcriptase from Feline Immunodeficiency Virus Confers Resistance to Oxathiolane Nucleosides" *Journal of Virology*, 1997, pp. 2357–2362, vol. 71, No. 3.

Smyth, N. R. et al. "Susceptibility in Cell Culture of Feline Immunodeficiency Virus to Eighteen Antiviral Agents" *Journal of Antimicrobial Chemotherapy*, 1994, pp. 589–594, vol. 34.

Smyth, N. R. et al. "Effect of 3'Azido–2',3'–Deoxythymidine (AZT) on Experimental Feline Immunodeficiency Virus Infection in Domestic Cats" *Research in Veterinary Science*, 1994, pp. 220–224, vol. 57.

Tisdale, M. et al. "Rapid in Vitro Selection of Human Immunodeficiency Virus Type 1 Resistant to 3'–Thiacytidine Inhibitors Due to a Mutation in the YMDD Region of Reverse Transcriptase" *Proc. Natl. Acad. Sci. USA*, Jun. 1993, pp. 5653–5656, vol. 90.

Torres, R. A. et al. "Combination Antiretroviral Therapy for HIV Infection" *Infect. Med.*, Feb. 1997, pp. 142–160, vol. 14.

Wlodawer, A. et al. "Structure of an Inhibitor Complex of the Proteinase From Feline Immunodeficiency Virus" *Nature Structural Biology*, Jun. 1995, pp. 480–488, vol. 2, No. 6.

Yamamoto, J. et al. "Pathogenesis of Experimentally Induced Feline Immunodeficiency Virus Infection in Cats" *Am J Vet Res*, Aug. 1988, pp. 1246–1258, vol. 49, No. 8.

Yamamoto, J. et al. "Feline Immunodeficiency Syndrome—A Comparison Between Feline T–Lymphotropic Lentivirus and Feline Leukemia Virus" *Leukemia*, Dec. 1988, pp. 204S–215S, vol. 2, No. 12 Supplement.

* cited by examiner

COMBINATION THERAPY FOR TREATMENT OF FIV INFECTION

This application is a U.S. national stage application filed from international patent application No. PCT/US99/11940, filed May 28, 1999, which claims the benefit of U.S. provisional application Ser. No. 60/087,281, filed May 29, 1998, now abandoned.

BACKGROUND OF THE INVENTION

Feline immunodeficiency virus (FIV) is a lentivirus which causes immunodeficiency syndrome in domestic cats (Pedersen et al., 1987; Siebelink et al., 1990). FIV closely resembles human immunodeficiency virus (HIV) in genomic, biochemical, and morphologic characteristics as well as clinical and hematological manifestations (Johnson et al., 1994; Pedersen et al., 1987; Yamamoto, Sparger et al., 1988). As a result, FIV infection of domestic cats is considered to be an excellent small animal model for testing prophylactic and therapeutic strategies against AIDS viruses (Gardner, 1991; Johnson et al., 1994). A number of antiretroviral drugs for HIV, including the prototype nucleoside analogue azidothymidine (AZT), has been tested using the FIV model (Hart et al., 1995; Hartmaun et al., 1992; Hayees et al., 1993; Hayees et al., 1995; Meers et al., 1993; North et al., 1989; Smith et al., 1994).

The therapeutic use of AZT has been unremarkable in cats and was unable to delay the spread of FIV infection in vivo (Hart et al., 1995; Hartmaun et al., 1992).

Prophylactic AZT treatment of experimental cats caused either a delay or decrease in both infected blood lymphocyte numbers and plasma virus load (Hayees et al, 1993; Hayees et al., 1995; Meers et al., 1993; Smith et al., 1994). In addition, a delay in FIV antibody production was observed in some animals (Smith et al., 1994). However, prophylactic therapy with AZT did not protect cats from FIV infection (Meers et al., 1993; Hayees et al., 1993; Hayees et al., 1995; Smith et al., 1994). As reported for HIV therapy, withdrawal of the drug resulted in a resurgence of the virus in these cats. When compared to the untreated group, significantly higher CD4 and CD8 cell counts were observed shortly after the withdrawal of the drug (Hayees et al., 1993; Hayees et al., 1995). However, CD4/CD8 ratios were not significantly different from the untreated cats. In contrast, FIV-infected cats therapeutically treated with AZT had no change in FIV antigen or anti-FIV antibody titers but had transient improvement in CD4/CD8 ratios and clinical signs (Hart et al., 1995; Hartmaun et al., 1992). These findings suggest that monotherapy with AZT has limited benefit as a therapy for FIV infection. Similar observations have been made with AZT monotherapy of HIV-infected individuals (Harrigan, 1995; Staszewski, 1995).

In recent trials, combination therapies with AZT and other antiretroviral drugs, such as phosphonomethoxyethyl) adenine and dideoxycytidine 5'-triphosphate, had minimal to no effect in preventing or controlling FIV infection in cats (Hartmaun et al., 1992; Magnani et al., 1994; Philpott et al., 1992). The in vivo use of viral protease inhibitors or new nucleoside analogue combinations, such as, for example, lamivudine (3TC) and AZT has yet to be reported in FIV-infected cats. Commercially available HIV protease inhibitors (e.g., Sequinavir (SQV), Indinavir (IDV), Ritonavir, Nelfinavir) do not inhibit FIV replication in PBMC in vitro. Unlike other nucleoside analogues, 3TC rapidly induces mutations which can phenotypically reverse the mutations caused by AZT, enabling the antiviral activity of AZT to persist in the host (Boucher et al., 1993; Larder, 1995; Tisdale et al, 1993). This unique feature of 3TC makes it a prime candidate for use in combination with AZT. In HIV-positive individuals, the combination AZT/3TC therapy had synergistic or additive effects at decreasing plasma virus load and increasing CD4 cell counts and function (Katlama et al., 1994; Lange, 1995; Paul et al., 1995; Staszewski, 1995). The addition of an HIV protease inhibitor to this combination further decreased the viral load and improved the CD4 cell count (Deeks et al., 1997; Torres et al., 1997).

BRIEF SUMMARY OF THE INVENTION

The subject invention concerns methods for therapeutic and prophylactic treatment of feline animals against infection by FIV. Methods of the present invention utilize a combination of antiretroviral compounds. In one embodiment, an effective amount of a composition comprising AZT and another nucleoside such as 3TC. In another embodiment, cats are given an effective dose(s) of a composition comprising AZT, a nucleoside analog such as 3TC and a retroviral protease inhibitor. In an exemplified embodiment, the protease inhibitor is HBY-793 (Hoescht-Bayer).

The Day 9 and 12 harvest results for AZT/3TC/FIV-PI culture set were statistically different ($p<0.05$) from the results of AZT/3TC culture set and FIV-PI culture set from the same time points, as indicated by (Z) above AZT/3TC/FIV-PI bars (panel B).

FIG. 3 shows anti-FIV activities of AZT, 3TC, FIV-PI, and HIV-PI in primary PBMC infected with $FIV_{UK-8}$ (subtype A strain). Four separate experiments with varying concentrations and combinations were performed and the results from two representative experiments are shown. Nucleoside analogue and P1 doses were 0.1 $\mu M$ and 0.01–0.5 $\mu M$, respectively, in Experiment 1 (panel A) and 0.05 µM and 0.01–0.5 µM respectively, in Experiment 2 (panel B). The RT data are presented as % control and the results from treated culture sets which are statistically different from the values of the untreated controls are indicated by either p<0.05 (P) or p<0.005 (P*). Statistical differences existed between the results of AZT/3TC culture set and 3TC culture set at Harvest Days 17 (p<0.02) and 20 (p<0.001) in panel A and Harvest Days 9 (p<0.02), 12 (p<0.04), and 15 (p<0.02) in panel B, as indicated by (X) above the AZT/3TC bars. In addition, statistical difference existed between the results of AZT/3TC culture set and AZT culture set at Harvest Day 20 (p<0.001) in panel A and Harvest Day 15 (p<0.01) in panel B, as indicated by (Z) above the AZT/3TC bars.

Figure 4:
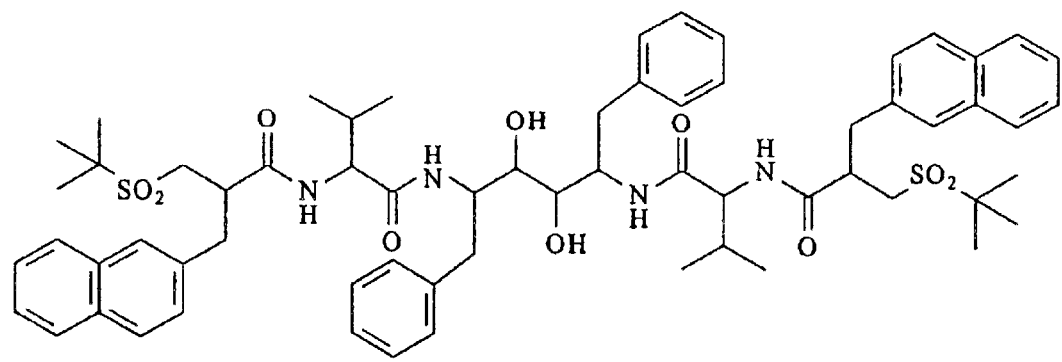

FIG. 4 shows the chemical structure of the protease inhibitor designated herein as HBY-793.

DETAILED DISCLOSURE OF THE INVENTION

The subject invention concerns methods for therapeutic and prophylactic treatment of cats against infection by FIV. Methods of the present invention utilize a combination of antiretroviral compounds. In one embodiment, cats can be administered an effective amount of a composition comprising AZT and another nucleoside analog.

Preferably, the nucleoside analog is 3TC.

In another embodiment of the methods of the present invention, cats are given an effective dose(s) of a composition comprising AZT, another nucleoside analog and a retroviral protease inhibitor. Preferably, the nucleoside analog is 3TC. In an exemplified embodiment, the protease inhibitor is HBY-793. The structure of HYB-793 is shown in FIG. 4. Other retroviral protease inhibitors that can inhibit FIV proteases are contemplated within the scope of this invention.

FIV-infected cats treated according to the methods of the present invention can also be given bone marrow transplantation after total body irradiation in conjunction with the antiretroviral drug combination therapy. The bone marrow transplanted can be either allogeneic or autologous.

The antiretroviral compositions of the subject invention can be administered using standard procedures known in the art. For example, the compositions can be administered as oral or nasal formulations. The compositions can also be administered by parenteral injection, i.e., intravenous, intramuscular, or subcutaneous injection. The amounts and dosage regimens for administration can readily be determined by the ordinarily skilled clinician.

Cats that are not infected with FIV can be treated according to the methods of the present invention to provide effective prophylactic treatment against FIV infection. FIV-infected cats can be treated according to the subject methods to provide effective therapy for controlling, inhibiting or eliminating FIV infection in that cat.

Results from studies described herein show that the addition of a nucleoside analog like 3TC to prophylactic AZT therapy will completely protect cats against FIV infection. This observation is supported by the in vitro findings demonstrating that an AZT/3TC combination was more effective at inhibiting FIV replication in PBMC cultures than single-drug treatments using AZT or 3TC alone. The AZT/3TC combination is effective when used prophylactically or immediately upon FIV exposure.

In addition, the combination of antiretroviral drugs AZT/3TC/FIV-PI can be used as an anti-FIV therapy to treat chronically infected animals.

The present invention also concerns kits comprising in one or more containers AZT, another nucleoside analog and an inhibitor of a retroviral protease. Preferably, the nucleoside analog is 3TC. In a preferred embodiment, the retroviral protease inhibitor is HBY-793.

The following abbreviations of FIV strains are used herein:

| Strain (subtype) | Abbreviation |
|---|---|
| Petaluma (A) | $FIV_{Pet}$ |
| Dixon (A) | $FIV_{Dix}$ |
| UK8 (A) | $FIV_{UK-8}$ |
| Bangston (B) | $FIV_{Bang}$ |
| Aomori-1 (B) | $FIV_{Aom1}$ |
| Aomori-2 (B) | $FIV_{Aom2}$ |
| Shizuoka (D) | $FIV_{Shi}$ |

All references cited herein are incorporated by reference.

Following are examples which illustrate procedures for practicing the invention.

These examples should not be construed as limiting. All percentages are by weight and all solvent mixture proportions are by volume unless otherwise noted.

EXAMPLE 1

In Vitro Efficacy of AZT, 3TC, and PI

Figure 1A:
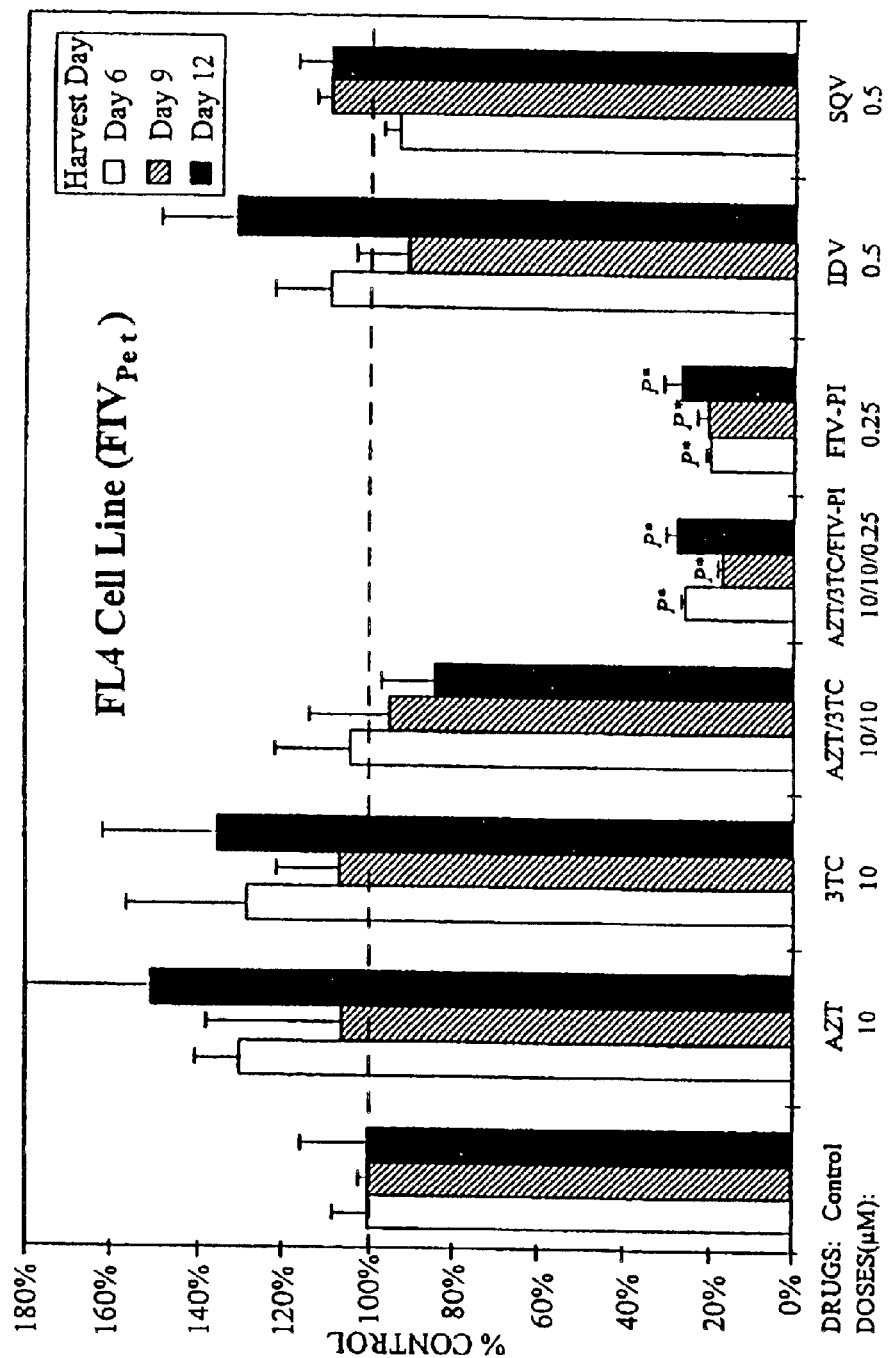
FIG. 1 shows anti-FIV activities of AZT, 3TC, FIV-PI, and HIV-PI (IDV and SQV) in chronically FIV-infected cell lines. The antiviral activity of the drugs at noncytotoxic doses were evaluated in feline T-cell lines chronically infected with either $FIV_{Pet}$ (subtype A strain) (panel A), or $FIV_{Bang}$ (subtype B strain) (panel B). The RT data are presented as % control, whereby % control represents RT mean of triplicate treated cultures divided by RT mean of triplicate untreated cultures and multiplied by 100. The RT data on harvest days at 6, 9, and 12 are shown. The results from treated culture sets which are statistically different from the values of the untreated controls are indicated by either $p<0.05$ (P) or $p<0.005$ (P*) based on Student T test.
Figure 1B:
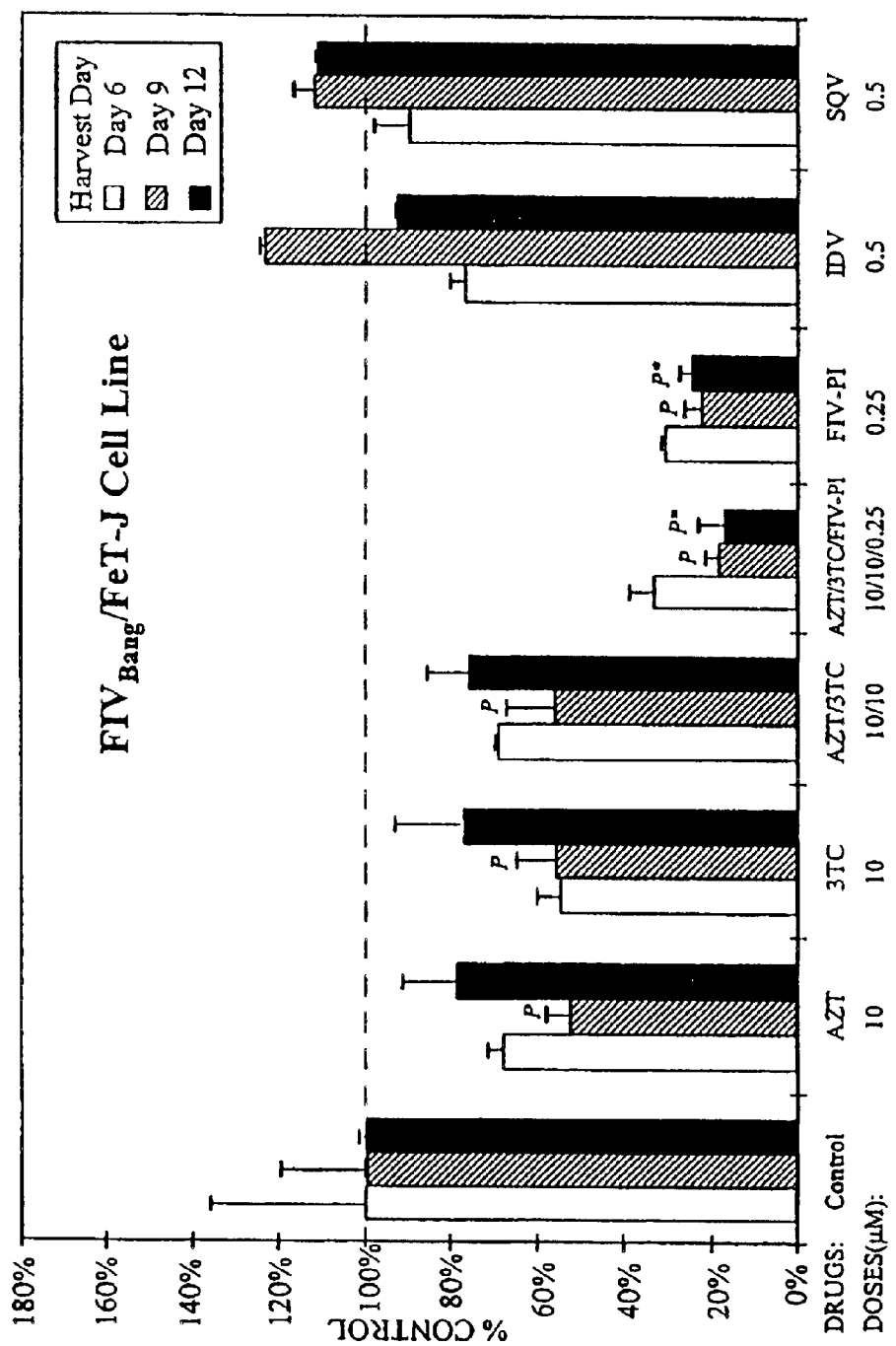

In the first set of in vitro studies, feline T-cell lines chronically infected with $FIV_{Pet}$, (FL-4 cells) or $FIV_{Bang}$, ($FIV_{Bang}$/FeT-J cells) at $2 \times 10^5$ cells/ml were treated for 3 weeks with a single drug or various combinations of AZT, 3TC, an FIV protease inhibitor (FIV-PI; Hoescht-Bayer HBY-793), and HIV protease inhibitors (HIV-PI) (FIGS. 1A and 1B). Saquinavir (SQV) and Indinavir (IDV) were used as the HIV-PIs. Culture supernatants were harvested and the cells were resuspended in fresh culture media containing appropriate drug(s) at 34 day intervals. Viral replication was determined by measuring the levels of reverse transcriptase (RT) activity in the culture supernatants (Rey et al., 1984). Drug toxicity in these cultures were monitored by viability and absolute cell count analyses using trypan blue exclusion method (Mishell et al., 1980).

Single and combination drug doses which were determined to be nontoxic to the test cells were used in these studies.

Both single and combination treatments with AZT and 3TC had minimal to no effect at inhibiting RT activity in $FIV_{Bang}$/FeT-J cells (20–50% inhibition) and FL-4 cells (0–10% inhibition). In contrast, FIV-PI treatment inhibited FIV replication by 70–80% in both cell lines (FIGS. 1A and 1B). However, the addition of an AZT/3TC combination did not enhance this inhibition. Furthermore, neither SQV nor IDV alone had significant anti-FIV effect (FIGS. 1A and 1B). The differences in anti-FIV activities of these nucleoside analogues and FIV-PI may be due to the differences in the mechanism(s) of their antiviral activities. AZT and 3TC exert their antiretroviral activity by preventing the reverse transcription of viral RNA into viral DNA, whereas FIV-PI prevents the production of a whole virion by inhibiting the FIV protease from cleaving viral gag-pro-pol precursor into their individual components. Therefore, cell lines which have proviral integration will not be affected by nucleoside analogues. Based on semi-quantitative PCR analysis, $FIV_{Bang}$/FeT-J cells and FL-4 cells used in current study had proviral integration of 50–80% and >95%, respectively (data not shown). The minor anti-FIV activity of AZT and 3TC observed in $FIV_{Bang}$/FeT-J cells may be due to the antiviral effect of the nucleoside analogues on the 20–50% of the cells which were still free of FIV proviral integration. As expected, potent anti-FIV activity was observed with FIV-PI in both proviral integrated cell lines.

Figure 2A:
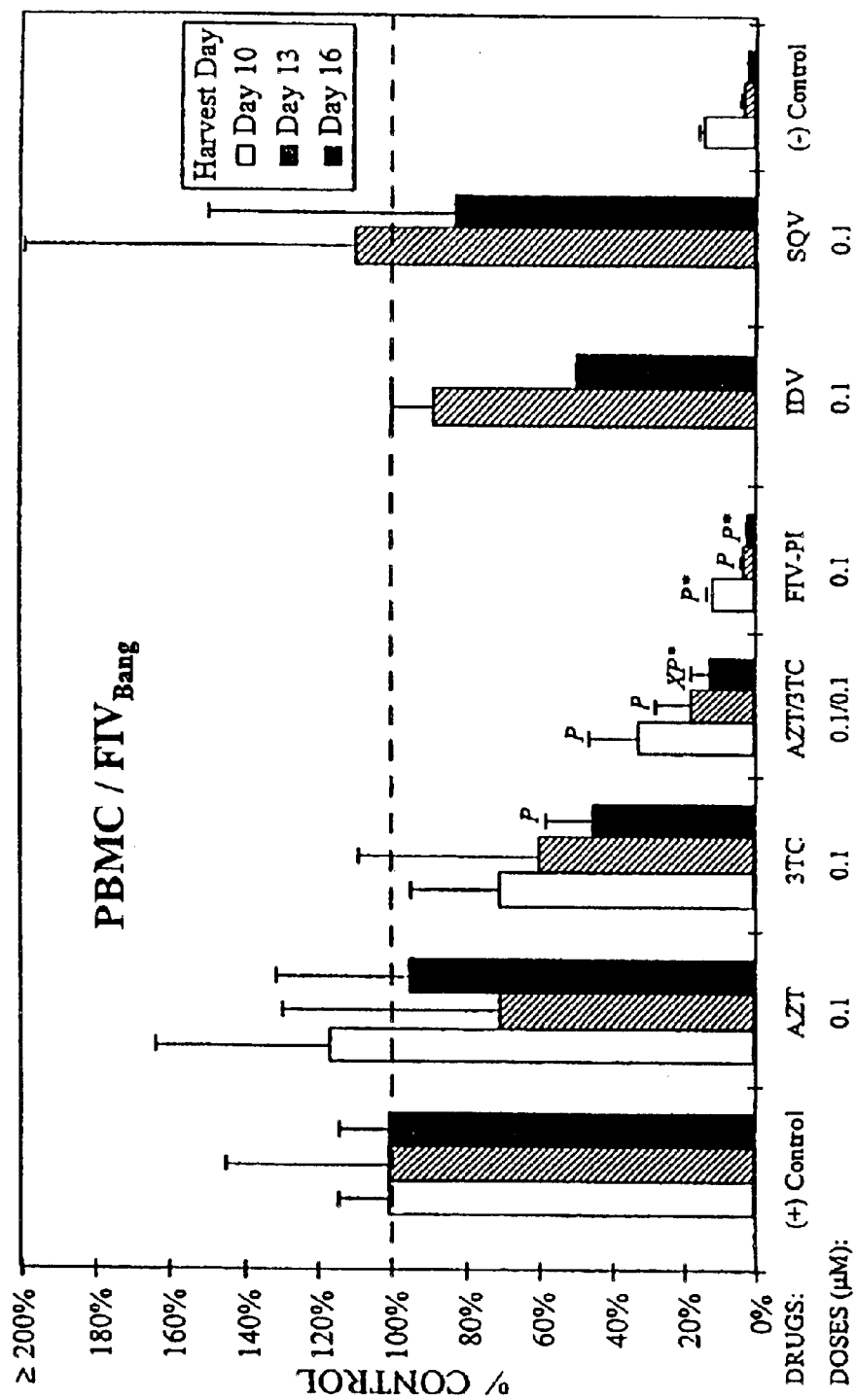
FIG. 2 shows anti-FIV activities of AZT, 3TC, FIV-PL and FIV-PI in primary PBMC infected with $FIV_{bang}$. Six separate experiments with varying concentrations and combinations were performed and the results from two representative experiments are shown. Nucleoside analogue and PI doses were 0.1 $\mu M$ in Experiment 1 (panel A) and 0.05 $\mu M$ and 0.01 $\mu M$, respectively, in Experiment 2 (panel B). The RT data are presented as % control and the results from treated culture sets which are statistically different from the values of the untreated controls are indicated by either $p<0.05$ (P) or $p<0.005$ (P*) based on Student T test. The Harvest Day 16 result for AZT/3TC culture set was statistically different ($p<0.03$) from the results of AZT culture set and 3TC culture set from the same time point, as indicated by (Y) above AZT/3TC bar (panel A).
Figure 2B:
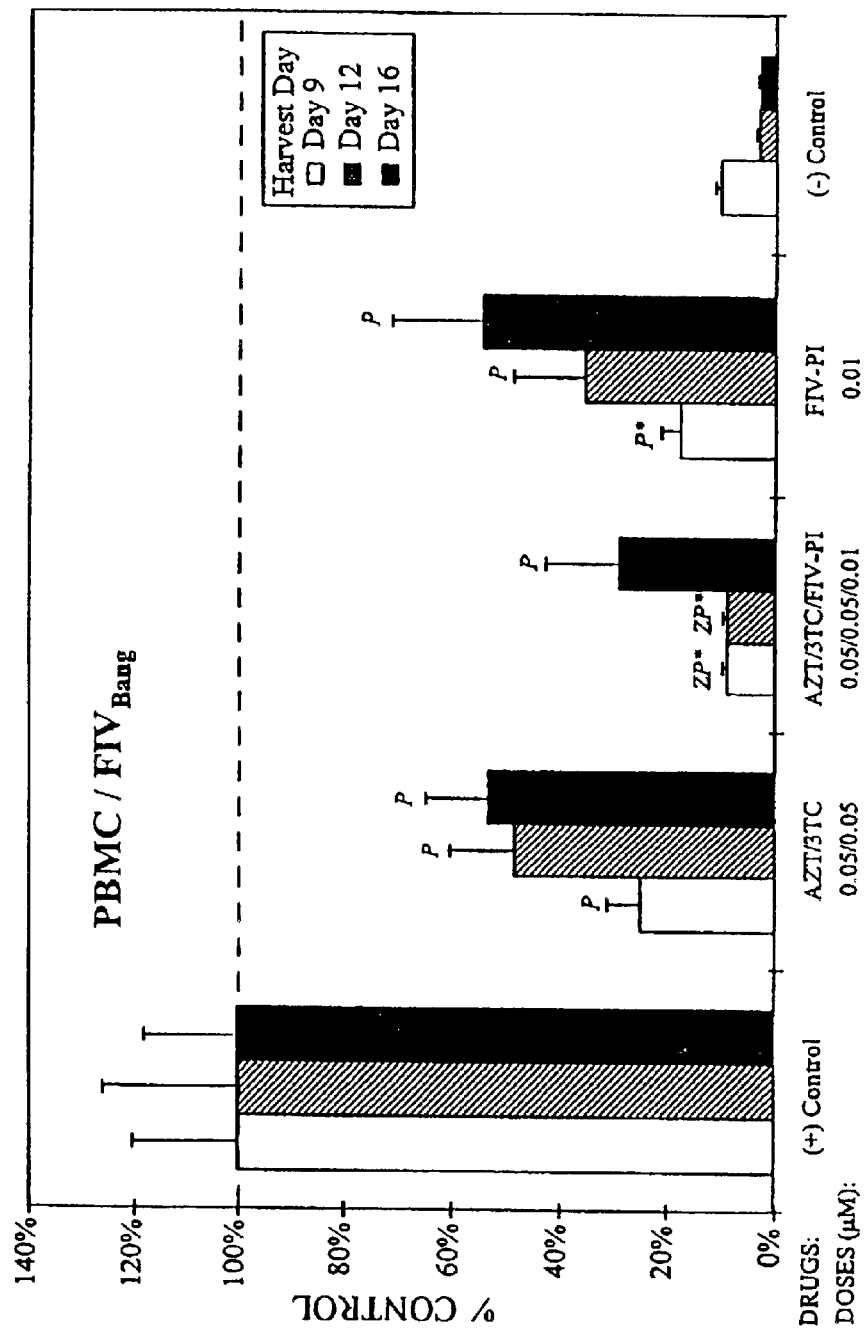
Figure 3A:
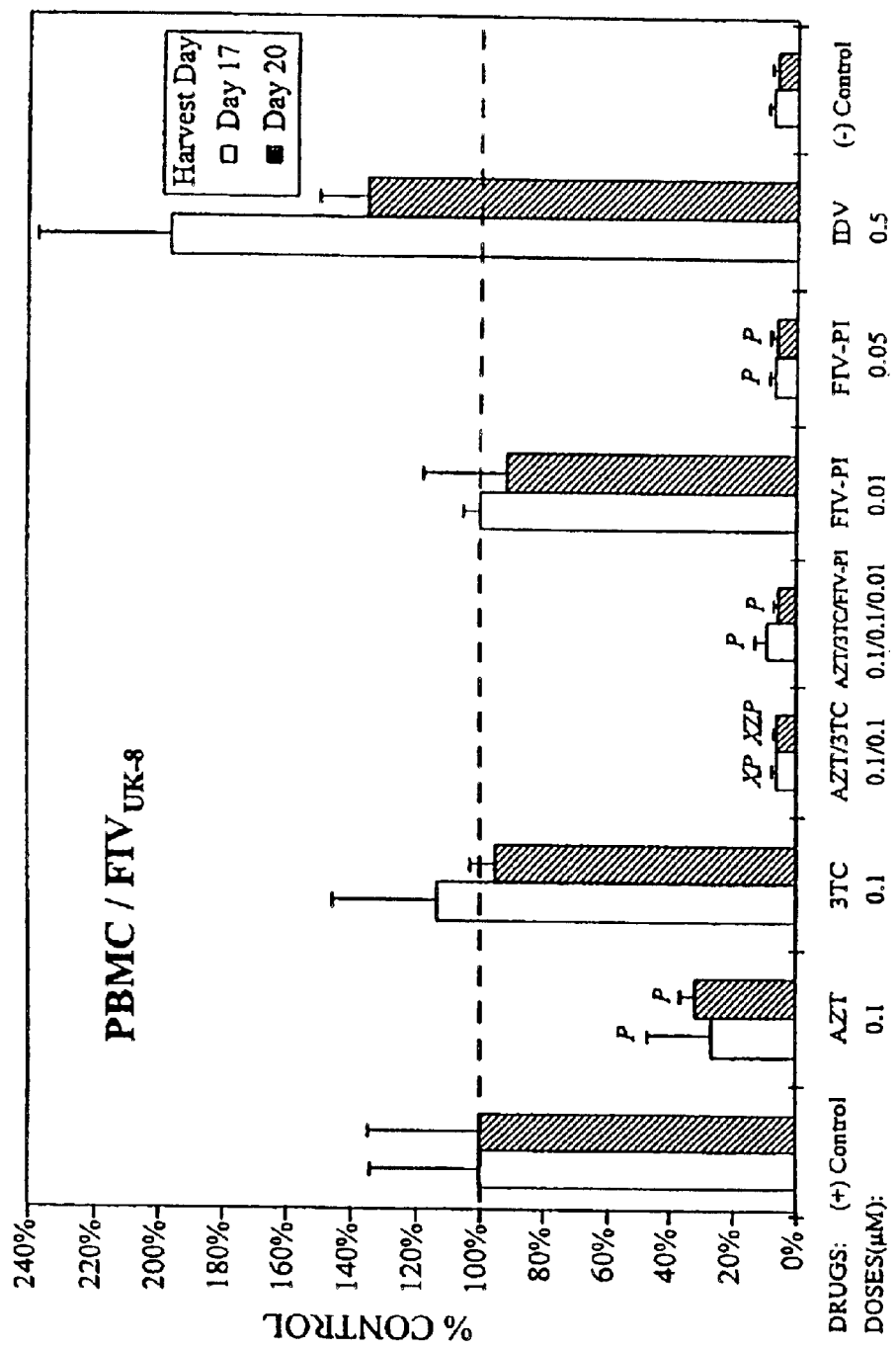
Figure 3B:
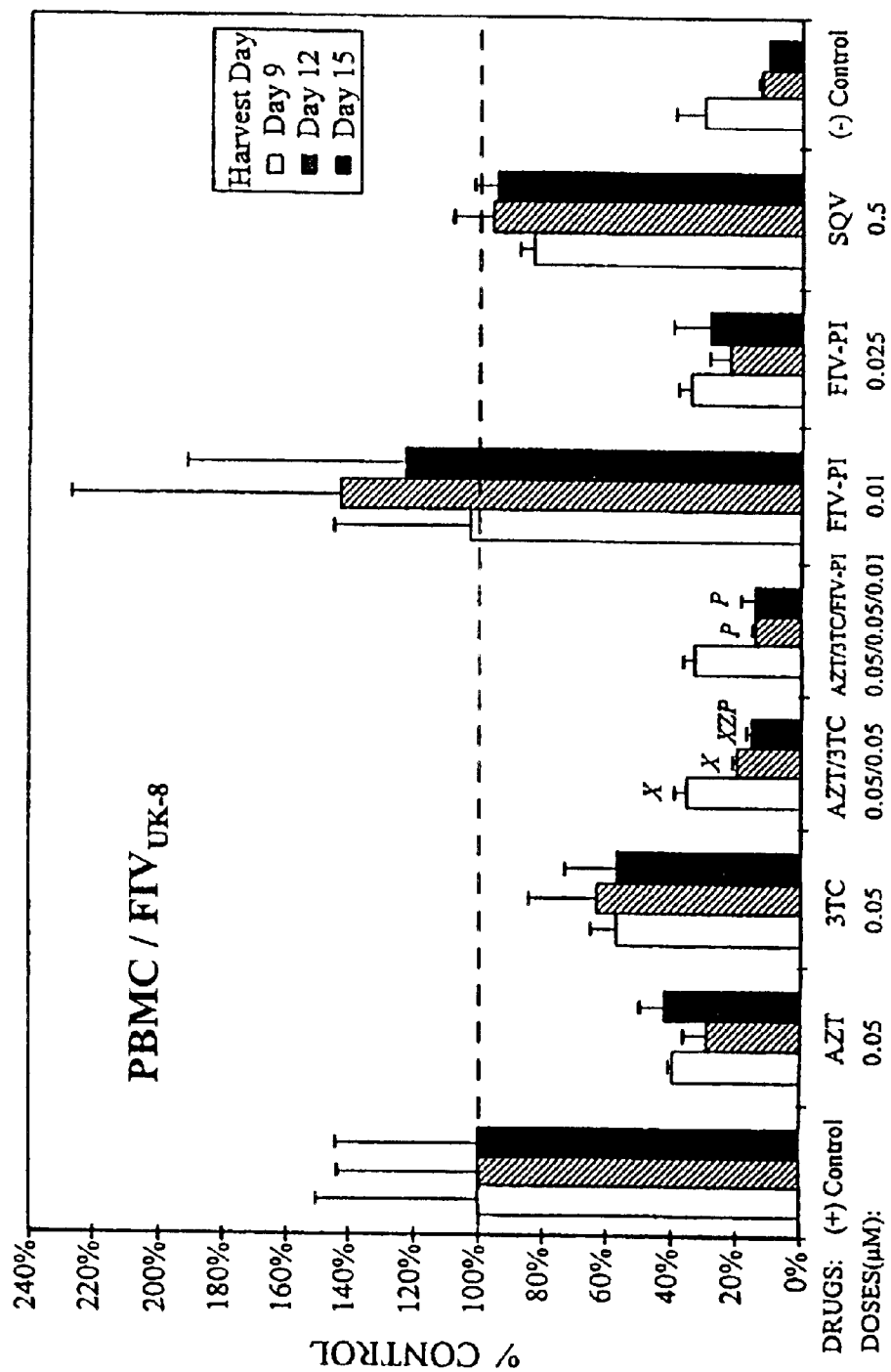

As a means to simulate in vivo conditions, primary peripheral blood mononuclear cells (PBMC) from specific pathogen free (SPF) cats were next used as the indicator cells. Primary PBMC isolated by ficoll hypaque method were stimulated with concanavalin A for 3 days and cultured for an additional 2 weeks before their use in drug studies (Staszewski, 1995). Antiretroviral drug(s) were added to the PBMC cultures ($1 \times 10^6$ cells/ml) immediately before $FIV_{Bang}$, (subtype B) or $FIV_{UK-8}$(subtype A) inoculation of 100 50% tissue culture infectious dose ($TCID_{50}$). Both single and combination treatments with AZT and 3TC inhibited the FIV replication in PBMC at doses which were not toxic to the cells (FIGS. 2A and 3A). Synergism in antiviral activities of AZT/3TC combination was observed against both $FIV_{Bang}$ and $FIV_{UK-8}$ strains (FIGS. 2A, 3A, and 3B). The addition of the FIV-PI to the AZT/3TC combination further enhanced the activities of these drugs against $FIV_{Bang}$(FIG. 2B). Such enhancement was not observed against $FIV_{UK-8}$ at the doses used (FIGS. 3A and 3B). Thus, the anti-FIV activities of AZT, 3TC, and FIV-PI are not restricted to specific FIV strain or subtype, although some strains appear to be more sensitive to one drug over another. Similar to previous studies with chronically infected cells, single-drug treatments with FIV-PI but not HIV-PIs (SQV and IDV) inhibited FIV replication in PBMC cultures (FIGS. 2A, 3A, and 3B). Furthermore, addition of SQV or IDV to the AZT/3TC combination did not enhance the antiviral activity of the AZT/3TC combination. The lack of anti-FIV activity of SQV and IDV may be explained by the fact that HIV-PIs do not efficiently bind to FIV protease, whereas the FIV-PI used in this study efficiently binds to HIV protease as well as FIV protease (Dunn et al., 1994; Wlodawer et al., 1995). These results show that dual and triple combinations of AZT, 3TC, and FIV-PI may have therapeutic benefit against FIV infection in domestic cats.

EXAMPLE 2

Prophylactic Efficacy of AZT/3TC in Cats

Based on the findings from in vitro studies, the prophylactic use of AZT/3TC combination was next tested in experimental cats. Four of the eight SPF cats (16–20 weeks of age) received oral administration of AZT and 3TC (75 mg/kg each) twice a day (BID), while remaining cats received placebo. This treatment dose was based on the in vivo research, in which six SPF cats (2 cats per treatment group) treated (BID) with either AZT or 3TC at 100 mg/kg or AZT/3TC combination at 50 mg/kg each had no hematological or clinical abnormalities after two weeks of treatment. In this study, all cats except for one treated cat (#RU1) were inoculated with 100 50% cat infectious dose ($CID_{50}$) of $FIV_{UK-8}$ sat 3 days after the first drug or placebo treatment. $FIV_{UK-8}$ was used in this study because this strain gave more consistent CD4/CD8 ratio inversion in a larger number of infected cats than did infection with $FIV_{Bang}$ or $FIV_{pet}$. All cats received either the drug or placebo treatments throughout the first 11 weeks after FIV inoculation, unless stated otherwise. The cats were monitored daily for clinical signs and twice a month for hematological changes, FIV load in PBMC and plasma, anti-FIV antibody titers, and CD4/CD8 ratio and absolute counts (Diehi et al., 1995; Green et al., 1993; Okada et al., 1994; Tellier et al., 1997; Yamamoto et al., 1991).

At 4 weeks of treatment, severe anemia was observed in all challenged and unchallenged cats treated with AZT/3TC; therefore, the doses of each drug were lowered to 34 mg/kg each at 4 weeks of treatment and subsequently to 5–10 mg/kg each at 5 weeks of treatment. AZT/3TC treatment was terminated in one cat (#3 GB) at 6 weeks of treatment, and the treatment was resumed 6 days later at 5 mg/kg each. Based on virus isolation and PCR analyses, one cat (#101) from the placebo group was positive for FIV by 3 weeks post infection (pi) and had anti-FIV antibodies by 5 weeks pi (Table 1).

However, plasma viral RNA levels of this cat were not detected throughout the study; even though the virus load in the PBMC was similar to the levels detected in the remaining placebo cats. These placebo cats (#NK4, #NK6, #IH5) were positive for FIV titers in the plasma and PBMC and for anti-FIV antibodies by 7 weeks pi. Furthermore, all placebo cats, except for cat #101, had transient or persistent CD4/CD8 inversion starting 11 weeks pi. In contrast, all AZT/3TC-treated cats were negative for FIV and had no CD4/CD8 inversion throughout the study. Both drug and placebo treatments were terminated at 11 weeks pi and all cats were monitored for additional 6–13 weeks. In the previous reports, an increase in FIV load of the PBMC was observed after the withdrawal of AZT treatment in FIV-infected cats (Hayees, et al., 1993; Hayees et al., 1995; Meers et al., 1993). Thus, if low levels of FIV infection undetectable by current assays existed in AZT/3TC-treated cats, then such infection should rebound when the drugs are removed. In this study, all AZT/3TC-treated cats remained negative for FIV in PBMC and anti-FIV antibodies throughout the 6–13 weeks after the withdrawal of the drug treatment. Virus isolation and PCR of bone marrow and lymph node cells performed at the termination of the study further confirmed the FIV-free status of these cats. Thus, complete protection of cats against experimental FIV infection was achieved with prophylactic AZT/3TC therapy.

EXAMPLE 3

Therapeutic Efficacy of AZT/3TC in Chronically FIV-Infected Cats

Based on the in vivo toxicity observed in the prophylactic study, three cats (#101, #NK6, #144) chronically infected with $FIV_{UK-8}$ for 16 weeks were treated at 20 mg/kg of each drug (BID), while an additional three infected cats (#1H5, #NK4, #158) received placebo. These cats were treated with either drug combination or placebo for 8 weeks and monitored an additional 4 weeks for changes in FIV load and CD4/CD8 values. All parameters monitored were identical to those of the prophylactic study. All treated cats developed either mild or severe anemia by 3.5 weeks of treatment. As a result, both drug doses were lowered to 10 mg/kg. Nevertheless, the anemia in one cat (#144) became so severe by 6 weeks of treatment that the drug treatment was terminated for 1 week and resumed thereafter at a low dose of 5 mg/kg of each drug (BID). Unlike the prophylactic study, no significant differences in either FIV load or CD4/CD8 ratios and absolute counts were observed between the treated and placebo cats (Table 2). This study in combination with the previous studies suggest that doses even as low as 20 mg/kg of each drugs when used over moderate period of time (3.5 weeks or longer) will cause anemia in cats. However, short-term treatment (2 weeks) with high dose combination (75 mg/kg each) is well tolerated by cats.

EXAMPLE 4

Allogeneic bone marrow transplantation (BMT) in combination with total body irradiation (TBI) and anti-FIV drug therapy was evaluated as an immune reconstitution therapy for FIV-infected cats. The rationale for this therapy is as follows: (1) TBI will decrease FIV load by destroying recipient's hematopoietic cells, including FIV-infected immunocytes. (2) Anti-FIV drug therapy can block the infection of engrafted donor cells in the BMT recipients. (3) BMT with donor BM cells from uninfected cats will reconstitute normal hematopoietic system. The TBI/BMT combination alone was unable to decrease the virus load due to rapid infection of engrafted donor cells. A majority of FIV-infected recipients of allogeneic BMT succumbed to graft-versus-host disease, accelerated FIV-related diseases, or their combination. As a result, studies were performed to identify antiretroviral drugs that can be combined with TBI/BMT.

Prophylactic therapy with AZT/3TC combination protected 100% of the cats from $FIV_{UK-8}$ challenge infection. Moreover, the only FIV-infected cat to survive allogeneic BMT also received concurrent AZT/3TC therapy. This cat had complete hematopoietic engraftment including normal CD8 counts. However, its CD4 counts were only slightly higher than the levels observed before BMT. Furthermore, only slight decrease in plasma virus load was observed during high-dose AZT/3TC therapy. Nonetheless, its anti-FIV antibody titers were 100-fold lower than those before BMT. This cat was still healthy at one year post-BMT and is still responsive to AZT/3TC therapy.

EXAMPLE 5

Recent findings with anti-HIV triple-drug combination have revealed that triple-drug cocktails are unable to immune reconstitute the patient with normal numbers and repertoire of T cell populations or to completely decrease/remove the virus load in the lymphoid tissues within feasible duration of time. As such, autologous bone marrow transplantation (BMT) was tested in combination with antiretroviral drugs as an immune reconstitution therapy for FIV-infected cats. Based on preliminary results, no significant decrease in FIV load or improvement in CD4/CD8 ratios or counts were detected in infected cats that received autologous BMT one (1) day after total body irradiation (TBI).

These cats survived the autologous BMT and are currently alive over two years after BMT. This is in contrast to the results from allogeneic BMT of FIV-infected cats, whereby all cats except the one on AZT/3TC therapy succumbed to GVHD, accelerated FIV-disease, or their combination. The extension of the time of BMT after TBI will decrease the infected cell reservoir load and, consequently, fewer infected cells will be available to infect engrafted cells. Addition of antiretroviral drug therapy will prevent any remaining infected cell reservoir from contaminating the engrafted cells.

EXAMPLE 6

Pharmaceutical Compositions

Antiviral compounds of the invention can be formulated according to known methods for preparing pharmaceutically useful compositions. *Remington's Pharmaceutical Science* by E. W. Martin describes formulations which can be used in connection with the subject invention. In general, the compositions of the subject invention will be formulated such that an effective amount of the antiviral compounds are is combined with a suitable carrier in order to facilitate effective administration of the composition. It should, of course, be understood that the compositions and methods of this invention may be used in combination with other therapies.

The compositions used in these therapies may also be in a variety of forms.

These include, for example, solid, semi-solid, and liquid dosage forms, such as tablets, pills, powders, liquid solutions or suspensions, liposomes, suppositories, injectable, and infusible solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose.

Once improvement in condition has occurred, a maintenance dose is administered if necessary. Subsequently, the dosage or the frequency of administration, or both, may be reduced, as a function of the symptoms, to a level at which the improved condition is retained.

It should be understood that the examples and embodiments described herein are for illustrative purposes only and that various modifications or changes in light thereof will be suggested to persons skilled in the art and are to be included within the spirit and purview of this application and the scope of the appended claims.

TABLE 1

AZT/3TC prophylaxis of cats starting 3 days before FIV inoculation

| Cat # | AZT/3TC treatment[a] (kg/mg) $-0.4 \rightarrow 4 \rightarrow 5 \rightarrow 6-7$ wk | FIV inocul. | FIV levels[b] VI/PCR/vRNA Pre | 4 wk | 9 wk | 11 wk | 14 wk | FIV antibodies[b] Pre | 4 wk | 9 wk | 11 wk | 14 wk | CD4/CD8 ratio[bc] Pre | 7 wk | 11 wk | 14 wk |
|---|---|---|---|---|---|---|---|---|---|---|---|---|---|---|---|---|
| DH5 | 75→34→10 | + | −/−/− | −/−/− | −/−/− | −/−/− | −/−/− | − | − | − | − | − | 3.30 | 2.86 | 2.62 | 2.38 |
| 3GB | 75→34→10→0-5 | + | −/−/− | −/−/− | −/−/− | −/−/− | −/−/− | − | − | − | − | − | 1.56 | 1.37 | 1.37 | 1.47 |
| RU2 | 75→34→10 | + | −/−/− | −/−/− | −/−/− | −/−/− | −/− | − | − | − | − | − | 1.77 | 1.21 | 1.18 | 1.18 |
| RU1 | 75→34→10 | − | −/−/− | −/−/− | −/−/− | −/−/− | −/−/− | − | − | − | − | − | 2.37 | 1.62 | 1.62 | 1.47 |
| NK4 | — | + | −/−/− | +/+/+ | +/+/+ | +/+/+ | +/+/+ | − | − | + | + | + | 1.82 | 1.55 | 0.96 | 0.91 |
| NK6 | — | + | −/−/− | −/+/+ | +/+/+ | +/+/+ | +/+/+ | − | − | + | + | + | 1.61 | 0.92 | 0.46 | 0.45 |

TABLE 1-continued

AZT/3TC prophylaxis of cats starting 3 days before FIV inoculation

| Cat # | AZT/3TC treatment[a] (kg/mg) −0.4→4→5→6–7 | FIV inocul. | FIV levels[b] VI/PCR/vRNA | | | | | FIV antibodies[b] | | | | | CD4/CD8 ratio[bc] | | | |
|---|---|---|---|---|---|---|---|---|---|---|---|---|---|---|---|---|
| | | | Pre | 4 wk | 9 wk | 11 wk | 14 wk | Pre | 4 wk | 9 wk | 11 wk | 14 wk | Pre | 7 wk | 11 wk | 14 wk |
| IO1 | — | + | −/−/− | +/+/− | +/+/− | +/+/− | +/+/− | − | − | + | + | + | 3.40 | 1.73 | 1.24 | 1.23 |
| IH5 | — | + | −/−/− | −/+/+ | +/+/+ | +/+/+ | +/+/+ | − | − | + | + | + | 4.40 | 1.34 | 0.60 | 0.61 |

[a]The AZT/3TC treatment was started 3 days before FIV inoculation (−0.4 post-infection) at a dose of 75 mg/kg each and decreased to 34 mg/kg at 4 wk post-infection (pi) and then to 10 mg/kg at 5 wk pi. In one cat (#3GB), the AZT/3TC treatment was withdrawn at 6 wk pi and resumed at a low dose of 5 mg/kg at 7 wk pi. The changes in doses if each drug, including the amount (mg/kg) and time (wk pi), are shown.
[b]Samples before drug or placebo treatment (Pre) and those at various weeks post-infection (wk) were tested for FIV levels, FIV antibodies, and CD4/CD8 rations. FIV levels were determined by virus isolation (VI), PCR for FIV provirus in PBMC, and RT-PCR for plasma viral RNA (vRNA). FIV antibodies were determined by immunoblot analysis. In general, RT-PCR for plasma viral RNA was less sensitive than PCR of FIV provirus in PBMC after amplification of infected cells by coculturing.
[c]Inverted CD4/CD8 ratios are bolded.

TABLE 2

AZT/3TC therapy of FIV-infected cats

| Cat No. | AZT/3TC treatment[a] (kg/mg) 0 wk→3.5 wk→6–7 wk | FIV load[b] (No. of infected cells in PBMC) | | | | FIV antibodies[b] | | | | CD4/CD8 ratio[b] | | | |
|---|---|---|---|---|---|---|---|---|---|---|---|---|---|
| | | 0 wk | 3.5 wk | 8 wk | 12 wk | 0 wk | 3.5 wk | 8 wk | 12 wk | 0 wk | 3.5 wk | 8 wk | 12 wk |
| 101 | 20→−10 | ++ | + | + | ++ | + | + | ++ | ++ | 1.45 | 1.58 | 1.71 | 1.71 |
| NK6 | 20→10 | ++ | ++ | + | + | ++ | ++ | ++ | ++ | 0.45 | 1.00 | 0.64 | 0.70 |
| 144 | 20→10→0–5 | +++ | ++++ | +++ | ++ | ++ | ++ | ++ | ++ | 0.67 | 0.74 | 0.45 | 0.52 |
| IH5 | — | ++ | ++ | + | ND | ++ | ++ | ++ | ++ | 0.61 | 0.63 | 0.73 | 0.87 |
| NK4 | — | ++ | + | + | + | + | ++ | ++ | ++ | 0.91 | 1.25 | 1.54 | 1.54 |
| 158 | — | +++ | +++ | +++ | ++ | + | ++ | ++ | ++ | 1.08 | 1.01 | 1.33 | 1.06 |

[a]The doses of each drug were decreased from 20 mg/kg to 10 mg/kg at 3 weeks treatment. Treatment was withdrawn in one cat (#144) at 6 weeks of treatment and resumed one week later at 5 mg/kg. The changes in doses of each drug, including amount (mg/kg) and time (wk after initial treatment), are shown.
[b]Samples before drug or placebo treatments (0 wk) and those at various weeks after initial treatment (wk) were tested for FIV levels, FIV antibodies, and CD4/CD8 ratios. FIV loads were determined by the number of PBMC (50 to $5 \times 10^6$ PBMC cocultured with $5 \times 10^6$ feeder PBMC) needed for positive virus isolation. Virus isolation results are presented as 50 (++++), $5 \times 10^2$ (+++), $5 \times 10^3$ (++), and $5 \times 10^4$ (+) PBMC from treated and untreated cats needed to isolate FIV from a culture containing $5 \times 10^6$ uninfected feeder PBMC. FIV antibody titer is defined as the minimal dilution (in $Log_{10}$) at which antibodies to FIV major core protein (p26) could be detected. Serial log dilutions of serum ($10^{-4}$ to $10^{-7}$ dilution) were incubated with immunoblot strip for 2 hrs and processed using the immunoblot method. End point titrations of FIV antibodies are presented as $10^{-5}$ (+) and $10^{-6}$ (++).

REFERENCES

Boucher, C. A. B., N. Cammack, P. Schipper, P. Rouse, M. A. Wainberg, and J. M.
  Cameron (1993) "High-level resistance to (−) enantiomeric 2-deoxy-3 thiacytidine in vitro is due to one amino acid substitution in the catalytic site in human immunodeficiency virus type 1 reverse transcriptase" *Antimicrob. Agents Chemother.* 37:2231–2234.
Deeks, S. G., M. Smith, M. Holodniy, J. O. Kahn (1997) "HIV-1 protease inhibitors" *J.*
  *Am. Med. Assoc.* 277:145–153.
Diehi, L. J., C. K. Mathiason-Dubard, L. L. O'Neil, and E. A. Hoover (1995) "Longitudinal assessment of feline immunodeficiency virus kinetics in plasma by use of a quantitative competitive reverse transcriptase PCR" *J. Virol.* 69:2328–2332.
Dunn, B. M., A. Gustchina, A. Wlodawer, and J. Kay (1994) "Subsite preference of retroviral proteinases" *Meth. Enzymol.* 241:254–278.
Gardner, M. B. (1991) "Mini-review. Simian and feline immunodeficiency viruses: animal lentivirus models for evaluation of AIDS vaccines and antiviral agents" *Antiviral Res.* 15:267–286.
Green, W. K, J. Meers, G. del Fierro, P. R. Carnegie, and W. F. Robinson (1993) "Extensive sequence variation of feline immunodeficiency virus env genes in isolates from naturally infected cats" *Arch. Virol.* 133:51–62.
Harrigan, R. (1995) "Measuring viral load in the clinical setting" *J. Acquir. Immune Deflc. Syndr. Hum Retrovirol.* 10(Suppl. 1):534–540.
Hart, S., and I. Nolte (1995) "Long-term treatment of diseased, FIV-seropositive field cats with azidothymidine (AZT)" *J. Vet. Med. A.* 42:397–409.
Hartnaun, K, A. Donath, B. Beer, H. F. Egberink, M. C. Horzinek, H. Lutz, G.
  Hoffrnann-Fezer, I. Thum, and S. Thefeld (1992) "Use of two virustatica (AZT, PMEA) in the treatment of FIV and of FeLV seropositive cats with clinical symptoms" *Vet. Immunol. Immunopathol.* 35:167–175.
Hayees, K. A., L. J. Lafrado, J. G. Erickson, J. M. Marr, and L. E. Mathes (1993) "Prophylactic ZDV therapy prevents early viremia and lymphocyte decline but not primary infection in feline immunodeficiency virus-inoculated cats" *J.*
  *Acquir. Immune Defic. Syndr.* 6:127–134.
Hayees, K. A., J. G. Wilkison, R. Frick, S. Francke, and L. E. Mathes (1995) "Early suppression of viremia by ZDV dose not alter the spread of feline immunodeficiency virus infection in cats" *J. Acquir. Immune Defic. Syndr. Hum. Retrovirol.* 9:114–122.
Johnson, M. C., B. A. Torres, H. Koyama, and J. K. Yamamoto (1994) "FIV as a model for AIDS vaccination" *AIDS Res. Hum. Retroviruses* 10:225–228.

Katlama, C., and the European Lainivudine Working Group (1994) "Combination 3TC (lamivudine)/ZVD (zidovudine) versus ZVD monotherapy in ZVD naive HTV-1positive patients with CD4 of 100–40Q cells/mm3, abstr" *AIDS* 8(Suppl. 4):56.

Lange, J. M. A. (1995) "Triple combinations: present and future" *J. Acquir. Immune Defic. Syndr. Hum. Retrovirol.* 10(Suppl. 1):577–582.

Larder, B. A. (1995) "Viral resistance and the selection of antiretroviral combinations" *J. Acquir. Immune Defic. Syndr. Hum. Retrovirol.* 10(Suppl.1):528–533.

Magnani, M., L. Rossi, A. Fraternale, L. Silvotti, F. Quintavalla, G. Piedimonte, D.

Matteucci, F. Baldinotti, and M. Bendinelli (1994) "Feline immunodeficiency virus infection of macrophages: In vitro and in vivo inhibition by dideoxycytidine-5'-triphosphate-loaded erythrocytes" *AIDS Res. Hum.*

Retroviruses 10:1179–1186.

Meers, J., G. M. del Fierro, I L B. Cope, H. S. Park, W. K Greene, and W. F. Robinson (1993) "Feline immunodeficiency virus infection: plasma, but not peripheral blood mononuclear cell virus titer is influenced by zidovudine and cyclosporine" *Arch. Virol.* 132:67–81.

Mishell, B. B., S. M. Shilgi, C. Henry, E. L. Chan, I. North, R. Gallily, M. Slomich, K Miller, I. Marbrook, D. Parks, and A. H. Good (1980) "Preparation of mouse cell suspensions" p.3–27. In B. B. Mishell and S. M. Shiigi (ed.), Selected methods in cellular immunology. W. H. Freeman and Co. San Francisco, Calif.

Newell, M. L., and D. M. Gibb (1995) "A risk-benefit assessment of zidovudine in the prevention of perinatal HIV trarisnussion" *Drug-Saf.* 12:274–282.

North, T. W., G. L. T. North, and N. C. Pedersen (1989) "Feline immunodeficiency virus, a model for reverse transcriptase-targeted chemotherapy for acquired inmmunedeficiency syndrome" *Antimicrob. Agents Chemother.* 33:915–919.

Okada, S., R. Pu, E. Young, W. Stoffs, and J. K. Yamamoto (1994) "Superinfection of cats with FIV subtypes A and B" *AIDS Res. Hum. Retroviruses* 10:1739–1746.

Paul, D. B., M. C. Kuhns, A. Al. McNamara, J. C. Jr. Pottage, and G. T. Spear (1995) "Short-term stability of HIV provirus levels in the peripheral blood of HIV-infected individuals" *J. Med. Virol.* 47:292–297.

Pedersen, N. C., E. W. Ho, M. L. Brown, and J. K. Yamamoto (1987) "Isolation of a lymphotropic virus from domestic cats with an immunodeficiency-like syndrome" *Science* 235:790–793.

Philpott, M. S., J. P. Ebner, and E. A. Hoover (1992) "Evaluation of 9-(2-phosphonylmethoxyethyl) adenine therapy for feline immunodeficiency virus using a quantitative polymerase chain reaction" *Vet. Immunol. Immunopathol.* 35:155–166.

Rey, M. A, B. Spire, D. Dormont, F. Barre-Sinoussi, L. Montagnier, and J. C. Chermann (1984) "Characterization of the RNA dependant DNA polymerase of new human T-lymphotropic retrovirus (lymphadenopathy associated virus)" *Biochem. Biophys. Res. Commun.* 21:1247–1253.

Siebelink, K. H. J., I—H, Chu, G. F. Rimmelzwaan, K. Weijer, R. V. Herwijnen, P. Kenell H. F. Egberrink, M. L. Bosch, and A. E. M. E. Osterhaus (1990) "Feline immunodeficiency virus (FIV) infection in the cats as a model for HIV infection in man: FIV-induced impairment of immune function" *AIDS Res. Hum. Retroviruses* 6:1373–1378.

Smith, N. R., M. Bennett, R. M. Gaskell, C. M. McCracken, C. A. Hart, and J. L. Howe (1994) "Effect of 3'azido-2'3'-deoxythymidine (AZT) on experimental feline immunodeficiency virus infection in domestic cats" *Res. Vet. Sci.* 57:220–224.

Staszewski, S. (1995) "Zidovudine and lamivudine: results of phase Ill studies" *J. Acquir. Immune Defic. Syndr. Hum Retrovirol.* 10(Suppl. 1):557.

Tellier, M. C., J. M. Soos, R. Pu, and J. K. Yamamoto (1997) "Development of FIV-specific cytolytic T-lymphocyte responses in cats upon immunization with FIV vaccines" *Vet. Microbiol.* 57:1–11.

Tisdale, M., S. D. Kemp, N. R. Parry, and B. A. Larder (1993) "Rapid in vitro selection of human immunodeficiency virus type 1 resistant to 3-thiacytidine inhibitors due to a mutation in the YMDD region of reverse transcriptase" *Proc Natl. Acad. Sci USA* 90:5663–5666.

Torres, R. A. and M. R. Barr (1997) "Combination antiretroviral therapy for HIV infection" *Infect. Med.* 14:142–160.

Wlodawer, A., A. Gustchina, L. Reshetnikova, J. Lubkowski, A. Zdanov, K. Y. Hui, E. L. Angleton, W. G. Farmerie, M. M. Goodenow, D. Bhatt, L. Zhang, and B. M. Dunn. (1995) "Structure of an inhibitor complex of the protease from feline immunodeficiency virus" *Nature Struct. Biol.* 2:480–488.

Yamamoto, J. K., T. Okuda, C. D. Ackley, H. Loule, H. Zochlinski, E. Pembroke, and M. B. Gardner (1991) "Experimental vaccine protection against feline immunodeficiency virus" *AIDS Res. Hum. Retroviruses* 7:911–922.

Yamamoto, J. K., N. C. Pedersen, E. W. Ho, T. Okuda, and G. H. Theilen (1988) "Feline immunodeficiency syndrome-A comparison between feline T-lymphotropic lentivirus and feline leukemia virus" *Leukemia* 2(Suppl. 12):2045–2155.

Yamamoto J. K., E. Sparger, E. W. Ho, P. R. Andersen, T. P. O'Connor, C. P. Mandell, L. Lowenstine, R. Munn, and N. C. Pedersen (1988) "Pathogenesis of experimentally induced feline immunodeficiency virus infection in cats" *Am. J. Vet. Res.* 49:1246–1258.

What is claimed is:

1. A method for treating infection by feline immunodeficiency virus (FIV) in a feline animal, said method comprising administering to said feline animal an effective amount of azidothymidine (AZT) and the nucleoside analog lamivudine (3TC) and wherein said feline animal receives allogeneic bone marrow transplantation after total body irradiation.

2. A method for treating infection by feline immunodeficiency virus (FIV) in a feline animal, said method comprising administering to said feline animal an effective amount of azidothymidine (AZT), the nucleoside analog lamivudine (3TC) and an inhibitor of a retroviral protease, and wherein said feline animal receives allogeneic bone marrow transplantation after total body irradiation.

3. The method according to claim 2, wherein said inhibitor of a retroviral protease is selected from the group consisting of HIV protease inhibitors and FIV protease inhibitors.

4. The method according to claim 2, wherein said inhibitor of a retroviral protease is designated as HBY-793 and has the structure shown in FIG. 4.

5. The method according to claim 1, wherein said azidothymidine or said nucleoside analog 3TC is administered as an oral or nasal formulation.

6. The method according to claim 1, wherein said azidothymidine or said nucleoside analog 3TC is administered by intravenous, intramuscular, or subcutaneous injection.

7. The method according to claim 1, wherein said azidothymidine or said nucleoside analog 3TC is administered in a dosage form selected from the group consisting of tablet, pill, powder, liquid solution or suspension, liposome, suppository, injectable, and infusible solution.

8. The method according to claim 1, wherein said FIV is a strain of FIV selected from the group consisting of $FIV_{Pet}$, $FIV_{DIX}$, $FIV_{UK-8}$, $FIV_{Bang}$, $FIV_{Aom1}$, $FIV_{Aom2}$, and $FIV_{Shi}$.

9. The method according to claim 2, wherein said azidothymidine, said nucleoside analog 3TC, or said retroviral protease inhibitor is administered as an oral or nasal formulation.

10. The method according to claim 2, wherein said azidothymidine, said nucleoside analog 3TC, or said retroviral protease inhibitor is administered by intravenous, intramuscular, or subcutaneous injection.

11. The method according to claim 2, wherein said azidothymidine, said nucleoside analog 3TC, or said retroviral protease inhibitor is administered in a dosage form selected from the group consisting of tablet, pill, powder, liquid solution or suspension, liposome, suppository, injectable, and infusible solution.

12. The method according to claim 2, wherein said FIV is a strain of FIV selected from the group consisting of $F_{Pet}$, $FIV_{Dix}$, $FIV_{UK8}$, $FIV_{Bang}$, $FIV_{Aom1}$, $FIV_{Aom2}$, and $FIV_{Shi}$.

13. The method according to claim 1, wherein said bone marrow transplant comprises autologous bone marrow.

14. The method according to claim 2, wherein said bone marrow transplant comprises autologous bone marrow.

* * * * *

UNITED STATES PATENT AND TRADEMARK OFFICE
CERTIFICATE OF CORRECTION

PATENT NO. : 6,875,773 B1
DATED : April 5, 2005
INVENTOR(S) : Dunn et al.

It is certified that error appears in the above-identified patent and that said Letters Patent is hereby corrected as shown below:

Column 2,
Line 40, "FIV-PL" should read -- FIV-PI --.

Column 4,
Line 31, "FIV$_{Pet}$," should read -- FIV$_{Pet}$ --.
Line 31, "FIV$_{Bang}$," should read -- FIV$_{Bang}$ --.

Column 5,
Line 16, "FIV$_{Bang}$," should read -- FIV$_{Bang}$ --.
Line 59, "Sat 3" should read -- at 3 --.

Column 9,
Line 44, "P. Schipper, P. Rouse" should read -- P. Schipper, R. Schuurman, P. Rouse --.
Line 47, "2-deoxy-3" should read -- 2'-deoxy-3' --.
Line 48, "in human" should read -- of human --.
Line 60, "preference" should read -- preferences --.

Column 10,
Line 45, "*Deflc.*" should read -- *Defic.* --.
Line 46, "10(Suppl. 1):534-540" should read -- 10(Suppl. 1):S34-S40 --.
Line 49, "Hartnaun" should read -- Hartmann --.
Line 65, "Johnson, M. C." should read -- Johnson, C.M. --.

Column 11,
Line 1, "Lainivudine Working" should read -- Lamivudive HIV Working --.
Line 8, "10(Suppl. 1):577-582" should read -- 10(Suppl. 1):S77-S82 --.
Line 11, "10(Suppl. 1):528-533" should read -- 10(Suppl. 1):S28-S33 --.
Line 19, "I L B. Cope" should read -- R. B. Cope --.
Line 41, "A. Al. McNamara" should read -- A. L. McNamara --.
Line 46, "a lymphotropic" should read -- a T-lymphotropic --.
Line 61, "A. E. M. E. Osterhaus" should read -- A.D.M.E. Osterhaus --.
Line 66, "Smith, N.R." should read -- Smyth, N.R. --.

UNITED STATES PATENT AND TRADEMARK OFFICE
CERTIFICATE OF CORRECTION

PATENT NO. : 6,875,773 B1
DATED : April 5, 2005
INVENTOR(S) : Dunn et al.

It is certified that error appears in the above-identified patent and that said Letters Patent is hereby corrected as shown below:

<u>Column 12,</u>
Line 15, "90:5663-5666" should read -- 90:5653-5656 --.
Line 23, "protease" should read -- proteinase --.
Line 34, "2045-2155" should read -- 204S-215S --.

Signed and Sealed this

Ninth Day of August, 2005

JON W. DUDAS
*Director of the United States Patent and Trademark Office*

UNITED STATES PATENT AND TRADEMARK OFFICE
CERTIFICATE OF CORRECTION

PATENT NO.     : 6,875,773 B1
DATED          : April 5, 2005
INVENTOR(S)    : Dunn et al.

It is certified that error appears in the above-identified patent and that said Letters Patent is hereby corrected as shown below:

Column 2,
Line 40, "FIV-PL" should read -- FIV-PI --.

Column 4,
Line 31, "$FIV_{Pet}$," should read -- $FIV_{Pet}$ --.
Line 31, "$FIV_{Bang}$," should read -- $FIV_{Bang}$ --.

Column 5,
Line 16, "$FIV_{Bang}$," should read -- $FIV_{Bang}$ --.
Line 59, "Sat 3" should read -- at 3 --.

Column 9,
Line 44, "P. Schipper, P. Rouse" should read -- P. Schipper, R. Schuurman, P. Rouse --.
Line 47, "2-deoxy-3" should read -- 2'-deoxy-3' --.
Line 48, "in human" should read -- of human --.
Line 60, "preference" should read -- preferences --.

Column 10,
Line 45, "*Deflc.*" should read -- *Defic.* --.
Line 46, "10(Suppl. 1):534-540" should read -- 10(Suppl. 1):S34-S40 --.
Line 49, "Hartnaun" should read -- Hartmann --.
Line 65, "Johnson, M. C." should read -- Johnson, C.M. --.

Column 11,
Line 1, "Lainivudine Working" should read -- Lamivudine HIV Working --.
Line 8, "10(Suppl. 1):577-582" should read -- 10(Suppl. 1):S77-S82 --.
Line 11, "10(Suppl. 1):528-533" should read -- 10(Suppl. 1):S28-S33 --.
Line 19, "I L B. Cope" should read -- R. B. Cope --.
Line 41, "A. Al. McNamara" should read -- A. L. McNamara --.
Line 46, "a lymphotropic" should read -- a T-lymphotropic --.
Line 61, "A. E. M. E. Osterhaus" should read -- A.D.M.E. Osterhaus --.
Line 66, "Smith, N.R." should read -- Smyth, N.R. --.

UNITED STATES PATENT AND TRADEMARK OFFICE
CERTIFICATE OF CORRECTION

PATENT NO. : 6,875,773 B1
DATED : April 5, 2005
INVENTOR(S) : Dunn et al.

It is certified that error appears in the above-identified patent and that said Letters Patent is hereby corrected as shown below:

<u>Column 12,</u>
Line 15, "90:5663-5666" should read -- 90:5653-5656 --.
Line 23, "protease" should read -- proteinase --.
Line 34, "2045-2155" should read -- 204S-215S --.

This certificate supersedes Certificate of Correction issued August 9, 2005.

Signed and Sealed this

Twenty-fifth Day of October, 2005

JON W. DUDAS
*Director of the United States Patent and Trademark Office*